United States Patent [19]

Ishitsuka et al.

[11] 4,352,792
[45] Oct. 5, 1982

[54] 3-ALKOXYFLAVONE ANTIVIRAL AGENTS

[75] Inventors: Hideo Ishitsuka, Yokohama; Haruyoshi Shirai, Isehara; Isao Umeda, Yokohama; Yasuji Suhara, Yokohama, all of Japan

[73] Assignee: Hoffmann-La Roche Inc., Nutley, N.J.

[21] Appl. No.: 137,637

[22] Filed: Apr. 7, 1980

[30] Foreign Application Priority Data

Apr. 10, 1979 [GB] United Kingdom ............... 7912610
Feb. 25, 1980 [GB] United Kingdom ............... 8006259

[51] Int. Cl.$^3$ .................... C07H 15/20; A61K 31/70
[52] U.S. Cl. .................................... 424/180; 424/283; 424/266; 536/8; 549/400; 546/269
[58] Field of Search .......................... 424/383, 180; 260/345.2; 536/8

[56] References Cited

U.S. PATENT DOCUMENTS

| 3,336,198 | 8/1967 | Mueller et al. ................. 536/8 |
| 3,974,184 | 8/1976 | Umezawa et al. ............. 260/345.2 |
| 4,105,781 | 8/1978 | Umio et al. ................... 260/345.2 |
| 4,150,038 | 4/1979 | Wingard ....................... 260/345.2 |
| 4,163,746 | 8/1979 | Feuer et al. .................. 260/345.2 |

FOREIGN PATENT DOCUMENTS

| 306716 | 4/1973 | Austria ....................... 260/345.2 |
| 1493546 | 5/1969 | Fed. Rep. of Germany ...... 536/8 |
| 1793025 | 2/1972 | Fed. Rep. of Germany ...... 536/8 |
| 2427597 | 4/1975 | Fed. Rep. of Germany ... 260/345.2 |
| 2740950 | 3/1979 | Fed. Rep. of Germany . |
| 1211311 | 11/1970 | United Kingdom ............ 260/345.2 |
| 1295606 | 11/1972 | United Kingdom ............ 260/345.2 |
| 1461777 | 5/1974 | United Kingdom ............ 260/345.2 |

OTHER PUBLICATIONS

Bahl et al., "*Current Sci.*" (India) 35, 281, 1966.
"Chem. Abst.", 65, 7132h, 1966.
Erdtman et al., "Tetrahedron Suppl." No. 8, 71–74, 1966.
"Chem. Abst." 66, 92415c, 1966.
Grover et al., "Indian J. Chem." 1, 382–385, 1963.
"Chem. Abst.", 60, 4094d, 1964.
Jurd, "Jour. Org. Chem.", 27, 1294–1297, 1962.
"Chem. Abst.", 57, 3396c, 1962.
Picker et al., "Aust. J. Chem." 26, 1111–1119, 1973.
"Chem. Abst." 78, 159343w, 1973.
Valesi et al., "Phytochemistry" 11, 2821–2826, 1972.
Yamaguchi, "Chem. Abst.", 56, 446d, 1960.
Derwent BO2 24096 B/13, 3/79.

*Primary Examiner*—Johnnie R. Brown
*Attorney, Agent, or Firm*—Jon S. Saxe; Bernard S. Leon; George W. Johnston

[57] ABSTRACT

Antiviral compositions containing 3-alkoxyflavone compounds as their active ingredients are disclosed.

67 Claims, 1 Drawing Figure

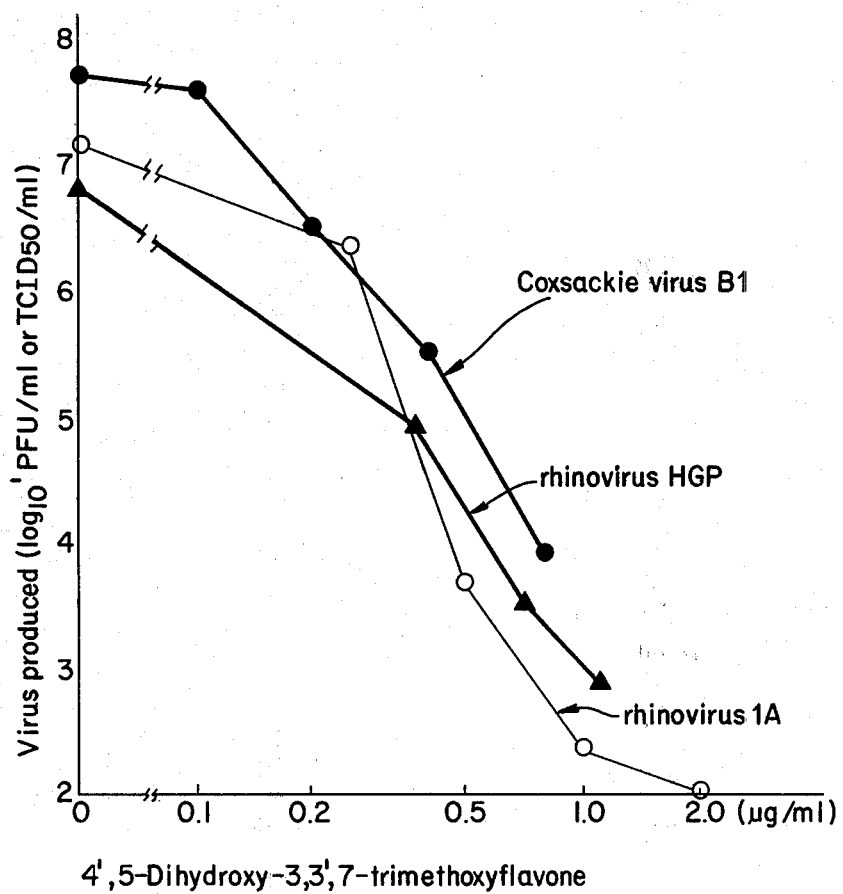

3-ALKOXYFLAVONE ANTIVIRAL AGENTS

SUMMARY OF THE INVENTION

The present invention concerns pharmaceutical compositions which are useful in treating mammals having infections caused by viruses such as human rhinoviruses, enteroviruses and influenzaviruses.

The antiviral compositions of the invention contain as active ingredients effective amounts of 3-alkoxyflavone compounds of the formula:

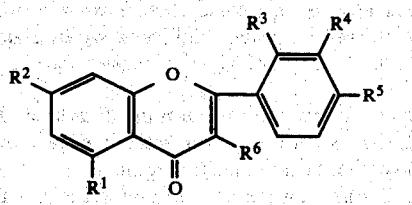

wherein $R^1$ is hydroxy, lower alkoxy, lower alkanoyloxy, alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy, glycosyloxy, a hydroxy-substituted dicarboxylic acid residue, amino, nicotinoyloxy or lowr alkoxycarbonyloxy and $R^6$ is lower alkoxy, or pharmaceutically acceptable salts thereof.

DETAILED DESCRIPTION OF THE INVENTION

The invention concerns 3-alkoxyflavone pharmaceutical compositions useful for treating mammals having infections caused by viruses such as human rhinoviruses, enteroviruses, influenzaviruses and the like. The invention also concerns novel 3-alkoxyflavone compounds which are useful as active antiviral ingredients in the inventive compositions.

As used herein, alkyl connotes straight or branched chain saturated aliphatic hydrocarbon groups containing 1 to 20 carbon atoms. Lower alkyl are alkyl groups of 1 to 6 carbon atoms such as methyl, ethyl, n-propyl, isopropyl and hexyl.

Alkoxy denotes straight or branched chain alkoxy groups of 1 to 20 carbon atoms. Lower alkoxy means alkoxy groups having 1 to 4 carbon atoms such as methoxy, ethoxy and isopropoxy.

Lower alkanoyloxy connotes alkanoyloxy groups of 2 to 7 carbon atoms such as acetoxy, propionyloxy, butyryloxy, isobutyryloxy and pivaloyloxy.

Lower alkoxycarbonyloxy denotes alkoxycarbonyloxy groups wherein its alkoxy moiety has 1 to 7 carbon atoms. Examples of lower alkoxycarbonyloxy groups are methoxycarbonyloxy, ethoxycarbonyloxy, isopropoxycarbonyloxy and hexyloxycarbonyloxy.

Aminoacyloxy denotes an organic radical derived from aliphatic amino acids of 2 to 10 carbon atoms by the removal of hydrogen from the hydroxy group of the acid. Among the preferred aliphatic amino acids are those which are saturated and monosubstituted. Preferred aminoacyloxy groups are L-lysyloxy, L-alanyloxy, L-glutaminyloxy and alpha-glutamyloxy.

Glycosyloxy connote radicals derived from monosaccharides of 5 to 7 carbon atoms by removal of the hydrogen from the anomeric hydroxy group of the monosaccharides. Preferred glycosyloxy groups are glucosyloxy, mannosyloxy, and galactosyloxy.

Reactive derivatives of a monosaccharide include glycosyl halides such as glycosyl chloride, glycosyl bromide and mannosyl bromide.

Lower alkanoic acids connote lower alkyl carboxylic acids such as acetic acid, isopropionic acid, hexanoic acid and the like. Reactive derivatives of lower alkanoic acids mean halides or anhydrides of the acids such as acetyl chloride, acetyl bromide and acetic anhydride.

Hydroxy-substituted dicarboxylic acid residues connote radicals of aliphatic hydroxy-substituted dicarboxylic acids wherein their aliphatic moieties contain from 2 to 8 carbon atoms. Among the preferred acids are saturated aliphatic hydroxy substituted dicarboxylic acids such as 1-hydroxy-1,2-ethanedicarboxylic acid and 1,2-dihydroxy-1,2-ethanedicarboxylic acid. Preferred hydroxy-substituted dicarboxylic acid residues are 3-carboxy-2-hydroxypropionyloxy and 3-carboxy-2,3-dihydroxypropionyloxy.

Alkali metals include lithium, sodium, potassium and rubidium. Alkali metal hydroxides include lithium hydroxide, sodium hydroxide and the like. Alkaline earth metals include barium, magnesium, calcium and strontium.

Diazoalkane connotes a group having an alkane moiety of 1 to 7 carbon atoms which is substituted with one diazo group. Examples of diazoalkanes are diazomethane diazopropane.

In accordance with the invention, applicants' antiviral composition has as an active ingredient a compound of the formula:

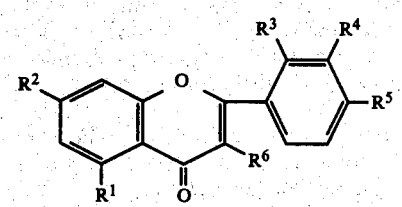

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy, glycosyloxy, a hydroxy-substituted dicarboxylic acid residue, amino, nicotinoyloxy or lower alkoxycarbonyloxy and $R^6$ is lower alkoxy.

Not all compounds within formula I are novel. Some are known to posses other than antiviral activity. The novel compounds within formula I, however, can be represented by a compound of the formula:

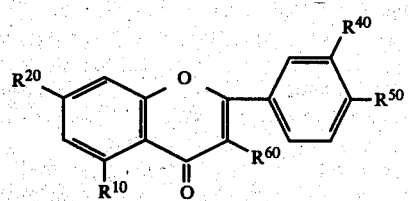

wherein $R^{10}$ is hydroxy, lower alkanoyloxy, lower alkoxycarbonyloxy or nicotinoyloxy; $R^{20}$ is hydroxy or lower alkoxy; $R^{40}$ is hydrogen or lower alkoxy; $R^{50}$ is hydroxy, lower alkanoyloxy, aminoacyloxy, glycosyloxy, a hydroxy-substituted dicarboxylic acid residue, amino nicotinoyloxy or lower alkoxycarbonyloxy and $R^{60}$ is lower alkoxy, with the proviso that when $R^{10}$ is acetoxy, $R^{50}$ is other than acetoxy and with the further proviso that when $R^{50}$ is hydroxy, $R^{60}$ is other than methoxy, or pharmaceutically acceptable salts thereof.

In an additional aspect of the invention, the substituents $R^{10}$–$R^{50}$ of formula II can be represented as follows: $R^{10}$ is hydroxy, lower alkanoyloxy, lower alkoxycarbonyloxy or nicotinoyloxy; $R^{20}$ is hydroxy or lower alkoxy; $R^{40}$ is hydrogen or lower alkoxy; $R^{50}$ is lower alkanoyloxy, aminoacyloxy, glycosyloxy, a hydroxy-substituted dicarboxylic acid residue, amino, nicotinoyloxy or lower alkoxycarbonyloxy, and $R^{60}$ is lower alkoxy, with the proviso that when $R^{10}$ is lower alkanoyloxy, $R^{50}$ is other than lower alkanoyloxy.

Alkali metal and alkaline earth metal salts of compounds I and II are included within the invention.

Representative compounds of formulas I and II are:
4'-acetoxy-5-hydroxy-3,3',7-trimethoxyflavone;
5-hydroxy-4'-(L-lysyloxy)-3,3',7-trimethoxyflavone;
4'-(β-D-glucopyranosyloxy)-5-hydroxy-3,3',7-trimethoxyflavone;
4'-(L-alanyloxy)-5-hydroxy-3,3',7-trimethoxyflavone;
4'-(L-glutaminyloxy)-5-hydroxy-3,3',7-trimethoxyflavone;
4'-(L-α-glutamyloxy)-5-hydroxy-3,3',7-trimethoxyflavone;
4'-(3-carboxy-2,3-dihydroxypropionyloxy)-5-hydroxy-3,3',7-trimethoxyflavone;
4'-amino-5,7-dihydroxy-3-methoxyflavone;
4'-amino-5-hydroxy-3,7-dimethoxyflavone;
3,3',7-trimethoxy-4',5-bis-(nicotinoyloxy)-flavone;
4',5-bis-(ethoxycarbonyloxy)-3,3',7-trimethoxyflavone;
5-hydroxy-3,3',7-trimethoxy-4'-(pivaloyloxy)-flavone;
5-(isobutyryloxy)-3,3',7-trimethoxy-4'-(pivaloyloxy)-flavone;
3,3',7-trimethoxy-4,',5-bis-(propionyloxy)-flavone;
3-ethoxy-4',5-dihydroxy-3',7-dimethoxyflavone;
4,',5-dihydroxy-3-isopropoxy-3',7-dimethoxyflavone;

Other representative compounds of formula I but not of formula II are:
4',5-dihydroxy-3,3',7-trimethoxyflavone;
4'-hydroxy-3,3'5,7-tetramethoxyflavone;
5,7-dihydroxy-3,4'-dimethoxyflavone;
3,'5-dihydroxy-3,4',7-trimethoxyflavone;
4,5-dihydroxy-3,7-dimethoxyflavone;
5-hydroxy-3,4',7-trimethoxyflavone;
4',5-dihydroxy-2',3,7-trimethoxyflavone;
4',5-diacetoxy-3,3',7-trimethoxyflavone.

The 3-alkoxyflavone compounds of formulas I and II exhibit antiviral activity and can be used as medicaments against viral diseases caused by rhinoviruses, enteroviruses, influenzaviruses and the like in the form of pharmaceutical preparations.

The pharmaceutical compositions of the invention contain at least one of the antiviral compounds of formula I and/or II in association with a compatible pharmaceutically acceptable carrier material. Any conventional carrier can be utilized. The carrier can be an organic or inorganic inert carrier material suitable for enteral, percutaneous or parenteral administration. Suitable carriers include water, gelatin, gum arabic, lactose, starch, magnesium stearate, talc, vegetable oils, polyalkyleneglycols, petroleum jelly and the like. Furthermore, the pharmaceutical preparations may contain other pharmaceutically active agents such as febrifuge, anodyne, anti-inflammatory, anti-histamine, interferon inducer and the like.

The pharmaceutical preparations can be made up in any conventional form including: (a) a solid form for oral administration such as tablets, capsules, pills, powders, granules and the like; (b) a liquid form for oral administration such as solutions, syrups, suspensions, elixirs and the like; (c) preparations for parenteral administration such as sterile solutions, suspensions or emulsions; and (d) preparations for topical administrations such as solutions, suspensions, ointments, micronized powders, aerosols and the like. The pharmaceutical preparations may be sterilized and/or may contain adjuvants such as preservatives, stabilizers, wetting agents, emulsifiers, salts for varying the osmotic pressure or buffers.

The active ingredients of formula I and/or II are present in the inventive compositions in an amount which is effective as an antiviral agent.

If desired, the pharmaceutical preparations can be administered so that the concentration of the active ingredient of the invention is greater than the minimum inhibitory concentration for the particular viral replication being treated.

The dosage for treatment depends on the route of administration, the age, weight and conditions of the patient and the particular disease to be treated. Typical dosages for adults are, for example, 100 to 1,000 mg. of the composition, 3 to 6 times daily for oral or parenteral administration and 0.1 to 100 μg of the compound/cm² of surface area, 3 to 6 times daily for topical administration.

In general, compounds, I and/or II amount to about 0.001% to about 70% by weight of the inventive compositions.

As previously mentioned, compounds I and II are useful in treating mammals having infections caused by viruses. To examine their antiviral activity, in vitro and in vivo experiments were performed on compounds I and II. The test result are summarized in Examples 24–32 below. It is found that compositions containing active ingredients of formula I and/or II inhibit the replication of human rhinoviruses and enteroviruses such as ECHO viruses, Coxsackie viruses, polioviruses and the like in human embryonic lung cell or HeLa cell cultures at doses of about 0.05 to about 10 μg of compound per ml. of pharmaceutical composition.

In addition to the above, compounds I and II of the invention are well tolerated and do not show any cytotoxicity at 10 to 100 times higher concentrations than their active dosages against viral infections. When administered orally to mice, said compounds do not show any toxic symptom at a dose of 5 g/kg. of body weight. See Example 32 below.

In accordance with a further aspect of the invention, compound I and/or II (or the above described pharmaceutical compositions containing same) can be administered to mammals such as humans to treat mammals having infections caused by viruses such as human rhinoviruses, enteroviruses, influenzaviruses and the like.

The compounds are administered in the aforementioned doses. In particular, the compounds of formulas I and II can be given at a daily dose of about 1 mg. to about 100 mg. of compound per kilogram of body weight of the mammal.

In a further aspect of the invention, the 3-alkoxyflavone compounds of formula I or II can be produced by:

(a) acylating the hydroxy group in position 40' or the hydroxy groups in positions 5 and 4' of a compound of the formula:

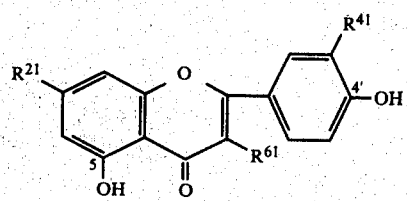

wherein $R^{21}$ is lower alkoxy; $R^{41}$ is hydrogen or lower alkoxy and $R^{61}$ is lower alkoxy, by treatment with a reactive derivative of a lower alkanoic acid, an aliphatic amino acid, a hydroxy-substituted dicarboxylic acid or nicotinic acid; or (b) glycosylating the hydroxy group in position 4' of compound III by treatment with a reactive derivative of a monosaccharide; or (c) reacting a 2',4', 6'-trihydroxy-2-alkoxyacetophenone with a bis-(4-acetamidobenzoic) anhydride and an alkali metal salt of 4-acetamidobenzoi acid and treating the resulting compound with an alkali metal hydroxide to yield 4'-amino-5,7-dihydroxy-3-alkoxyflavone, and, if desired, treating the resulting compound with a diazoalkane to form a corresponding 7-alkoxy compound.

The acylation in accordance with embodiment (a), the glycosylation in accordance with embodiment (b) and the reaction in accordance with embodiment (c) can be carried out in any conventional manner. Such techniques are illustrated in Examples 1-23.

Compounds of formula III are known or can be prepared from known compounds by conventional procedures.

The following Examples further illustrate the invention. All temperatures are in degrees Centigrade. Room temperature is about 23° C. Either connotes diethyl ether. Except for yield and unless otherwise stated, percentages are by volume. In the Examples, the term $LD_{50}$ means the amount (mg./kg. of body weight) of ingredient which would kill 50% of the test animals.

EXAMPLE 1

A mixture of 0.67 g of 2',6'-dihydroxy-2,4'-dimethoxyacetophenone, 3.5 g of bis-[4-(benzyloxy)-3-methoxybenzoic] anhydride and 1 g of sodium 4-(benzyloxy)-3-methoxybenzoate was heated at 180°–185° C. under reduced pressure for 3 hours. After cooling, 12 ml of 10% solution of potassium hydroxide in ethanol were added, and the mixture was refluxed under nitrogen for 30 minutes. To the cooled mixture were added 20 ml of 1 N-hydrochloric acid and 100 ml of chloroform, followed by shaking. The organic phase was separated and concentrated under reduced pressure. The residue was chromatographed on silica gel with chloroform. After recrystallization from ethyl acetate/hexane, there was obtained 0.86 g (60% yield) of 4'-(benzyloxy)-5-hydroxy-3,3',7-trimethoxyflavone as yellow crystals: m.p. 156°–157° C.

A solution of 0.86 g of 4'-(benzyloxy)-5-hydroxy-3,3',7-trimethoxyflavone in 30 ml of ethanol was hydrogenated in the presence of 50 mg of 5% by weight palladium-charcoal at room temperature under atmospheric pressure. After 1 hour, the catalyst was filtered off and the filtrate was evaporated under reduced pressure. The residue was recrystallized from ethyl acetate/hexane. There was obtained 0.58 g (90% yield) of 4',5-dihydroxy-3,3',7-trimethoxyflavone as yellow crystals: m.p. 171°–173° C.

EXAMPLE 2

In a manner analogous to that described in Example 1, from 2'-hydroxy-2,4',6'-trimethoxyacetophenone, there was obtained 4'-hydroxy-3,3',5,7-tetramethoxyflavone: m.p. 221°–223° C. (Yield: 24%).

EXAMPLE 3

Instead of the starting materials used in Example 1, 2',4',6'-trihydroxy-2-methoxyacetophenone, bis-(4-methoxybenzoic)-anhydride and sodium 4-methoxybenzoate were used and treated in a manner similar to that of Example 1. There was obtained 5,7-dihydroxy-3,4'-dimethoxyflavone: m.p. 238°–239° C. (Yield): 40%).

EXAMPLE 4

In a manner analogous to that described in Example 1 except that bis-[3-(benzyloxy)-4-methoxybenzoic]-anhydride and sodium 3-(benzyloxy)-4-methoxybenzoate were used, there was obtained 3',5-dihydroxy-3,4',7-trimethoxyflavone: m.p. 171° C. (Yield): 33%).

EXAMPLE 5

In a manner analogous to that described in Example 1 except that bis-(4-benzyloxybenzoic)-anhydride and sodium 4-benzyloxybenzoate were used, there was obtained 4',5-dihydroxy-3,7-dimethoxyflavone: m.p. 252°–253° C. (Yield: 23%).

EXAMPLE 6

In a manner analogous to that described in Example 1 except that bis-(4-methoxybenzoic)-anhydride and potassium 4-methoxybenzoate were used, there was obtained 5-hydroxy-3,4',7-trimethoxyflavone: m.p. 143°–145° C. (Yield 37%).

EXAMPLE 7

In a manner analgous to that described in Example 1 except that bis-[4-(benzyloxy)-2-methoxybenzoic]-anhydride and sodium 4-(benzyloxy)-2-methoxybenzoate were used, there was obtained 4',5-dihydroxy-2',3,7-trimethoxyflavone: m.p. 191°–192° (Yield 50%).

EXAMPLE 8

A mixture of 250 mg of 4',5-dihydroxy-3,3',7-trimethoxyflavone, 60 mg of sodium acetate and 70 mg of acetic anhydride was heated at 100° C. for 2 hours. The reaction mixture was evaporated under reduced pressure, and the residue was extracted with 30 ml of chloroform. Removal of the solvent from the extract and subsequent recrystallization of the residue from methanol gave 250 mg (90% yield) of 4'-acetoxy-5-hydroxy-3,3',7-trimethoxyflavone as yellow crystals: m.p. 168°–169° C.

EXAMPLE 9

A solution containing 460 mg of 4',5-dihydroxy-3,3',7-trimethoxyflavone and 600 mg of N,N'-di-(benzyloxycarbonyl)-L-lysine in 5 ml of pyridine was cooled to $-10°--5°$ C. To the solution was added 0.21 ml of thionyl chloride, while stirring over 5 minutes, and the mixture was allowed to stand at $-5°$ C. for 3 hours. Thirty ml of water were added thereto, and the mixture was extracted with 50 ml of chloroform. The extract was dried over anhydrous sodium sulfate and then concentrated under reduced pressure. The concentrate was applied onto a column of silica gel, and the column was eluted with chloroform to give 920 mg of N,N'-di-(benzyloxycarbonyl)-L-lysyl ester of 4',5-dihydroxy-3,3',7-trimethoxyflavone.

920 mg of said ester were dissolved in 3 ml of acetic acid containing 25% hydrogen bromide. After 45 minutes at a room temperature, the mixture was lyophilized to give 780 mg of 5-hydroxy-4'-(L-lysyloxy)-3,3',7-trimethoxyflavone. 2 HBR as pale yellow powder: m.p. 164° C. (dec.)

EXAMPLE 10

To an ice-cooled solution containing 250 mg of 4',5-dihydroxy-3,3',7-trimethoxyflavone in 10 ml of acetone were alternately added a solution of 400 mg of 2,3,4,6-tetra-O-acetyl-α-D-glucopyranosyl bromide in 10 ml of acetone, and 5 ml of 0.8% aqueous sodium hydroxide over 30 minutes, while stirring. After allowing the reaction mixture to stand at room temperature for 3 hours, 20 ml of 0.2% aqueous sodium hydroxide were added thereto. Stirring was continued at room temperature for 3 hours, during which time crystallization took place. The crystals were collected by filtration and recrystallized from ethanol to give 390 mg (80% yield) of 4'-(β-D-glucopyranosyloxy)-5-hydroxy-3,3',7-trimethoxyflavone as pale yellow needles: m.p. 203°–204° C.

EXAMPLE 11

A solution containing 500 mg of 4',5-dihydroxy-3,3',7-trimethoxyflavone and 360 mg of N-(benzyloxycarbonyl)-L-alanine in 5 ml of pyridine was cooled to $-10°--5°$ C. To the solution was added 0.38 g of thionyl chloride over 15 minutes, while stirring, and the reaction mixture was allowed to stand at $-5°$ C. for 3 hours. 30 ml of water were added, and the mixture was extracted with 50 ml of chloroform. The extract was dried over anhydrous sodium sulfate and then concentrated under reduced pressure. The concentrate was applied onto a column of silica gel, and the column was eluted with chloroform to yield 640 mg of N-(benzyloxycarbonyl)-L-alanyl ester of 4',5-dihydroxy-3,3',7-trimethoxyflavone.

640 mg of said ester were then dissolved in 3 ml of acetic acid containing 25% hydrogen bromide. The solution was allowed to stand at room temperature for 45 minutes and then lyophilized to give yellow powder which was then washed with three 10 ml portions of dichloromethane. The resulting insoluble material was dried over phosphorus pentoxide under reduced pressure to give 370 mg (64% yield) of 4'-(L-alanyloxy)-5-hydroxy-3,3',7-trimethoxyflavone hydrobromide: m.p. 201°–203° C.

EXAMPLE 12

A solution containing 500 mg of 4',5-dihydroxy-3,3',7-trimethoxyflavone and 450 mg of N-(benzyloxycarbonyl)-L-glutamine in 5 ml of pyridine was cooled to $-10°--5°$ C. To the solution were added 200 mg of thionyl chloride over 15 minutes, while stirring, and the reaction mixture was allowed to stand at $-5°$ C. for 3 hours. 30 ml of water were added, and said mixture was extracted with 50 ml of chloroform. The extract was dried over anhydrous sodium sulfate and then concentrated under reduced pressure. The concentrate was applied onto a column of silica gel, and the column was eluted with a mixed solvent of chloroform and methanol (9:1, v/v) to yield 830 mg of N-(benzyloxycarbonyl)-L-glutaminyl ester of 4',5-dihydroxy-3,3',7-trimethoxyflavone.

830 mg of said ester was dissolved in 3 ml of acetic acid containing 25% hydrogen bromide. The solution was allowed to stand at room temperature for 45 minutes and subjected to lyophilization, followed by washing with dichloromethane to give 750 mg (98% yield) of 4'-(L-glutaminyloxy)-5-hydroxy-3,3',7-trimethoxyflavone hydrobromide: m.p. 185°–188° C.

EXAMPLE 13

A solution containing 500 mg of 4',5-dihydroxy-3,3',7-trimethoxyflavone and 600 mg of 5-p-nitrobenzyl-N-(benzyloxycarbonyl)-L-glutamate in 5 ml of pyridine was cooled to $-10°--5°$ C. To the solution was added 0.17 g of thionyl chloride over 15 minutes, while stirring, and the reaction mixture was allowed to stand at $-5°$ C. for 3 hours. 30 ml of water were added thereto, and said mixture was extracted with 50 ml of chloroform. The extract was dried over anhydrous sodium sulfate and concentrated under reduced pressure. The concentrate was applied onto a column of silica gel, and the column was eluted with a mixed solvent of ethyl acetate and hexane (1:1, v/v) to yield 670 mg of pale yellow crystals.

670 mg of said crystals were dissolved in 50 ml of chloroform, and the solution was hydrogenated in the presence of 50 mg of palladium black at room temperature under atmospheric pressure for 3 hours. The catalyst was filtered off and the filtrate was evaporated to dryness. The residue was washed with 10 ml of dichloromethane and dissolved in 3 ml of acetic acid containing 25% hydrogen bromide. The solution was allowed to stand at room temperature for 45 minutes and subjected to lyophilization, followed by washing three times with 10 ml each of dichloromethane to give 370 mg (84% yield) of 4'-(L-α-glutamyloxy)-5-hydroxy-3,3',7-trimethoxyflavone hydrobromide: m.p. 243°–246° C.

EXAMPLE 14

A solution containing 500 mg of 4',5-dihydroxy-3,3',7-trimethoxyflavone, 470 mg of mono-p-methoxybenzyl ester of 2,3-O-isopropylidenetartaric acid and one drop of dimethylformamide in 5 ml of pyridine was cooled to $-10°--5°$ C. To the solution were added 170 mg of thionyl chloride over 15 minutes while stirring, and the mixture was kept at $-5°$ C. for 3 hours. 30 ml of water were added thereto and the mixture was extracted with 50 ml of chloroform. The extract was dried over anhydrous sodium sulfate, filtered, and the filtrate was concentrated. The concentrate was applied onto a column of silica gel, and the column was eluted with chloroform to yield 520 mg of pale yellow solid.

520 mg of said solid were dissolved in 50 ml of chloroform, and the solution was hydrogenated for 3 hours in the presence of 50 mg of palladium black at room temperature under atmospheric pressure. The catalyst was removed by filtration and the filtrate was evaporated to dryness. The residue was washed with dichloromethane and dissolved in 3 ml of acetic acid containing 25% of hydrogen bromide. The solution was allowed to stand at room temperature for 45 minutes, and the mixture was subjected to lyophilization, followed by washing three times with 10 ml each of dichloromethane to yield 280 mg (74% yield) of 4'-(3-carboxy- 2,3-dihydroxypropionyloxy)-5-hydroxy-3,3',7-trimethoxyflavone: m.p. 179°-180° C.

EXAMPLE 15

A mixture of 847 mg of 2',4',6'-trihydroxy-2-methoxyacetophenone, 5.82 g of bis-(4-acetamidobenzoic)-anhydride and 1.2 g of sodium 4-acetamidobenzoate was heated at 230° C. under reduced pressure for 3 hours. After cooling, 90 ml of methanol and 40 ml of 40% aqueous potassium hydroxide were added, and the mixture was refluxed for 1 hour. After removal of the methanol by evaporation under reduced pressure, the aqueous residue was diluted with 200 ml of water and the resulting suspension was filtered. The filtrate was saturated with carbon dioxide and the resulting suspension was extracted three times with 150 ml each of ethyl acetate. The combined extracts were washed with water, dried over anhydrous sodium sulfate and evaporated under reduced pressure to yield 460 mg of yellow residue.

460 mg of said residue were chromatographed on 15 g of silica gel. The column was eluted with ethyl acetate/hexane (1:1, v/v) and 120 ml of the eluate were evaporated under reduced pressure to give pale yellow residue. Recrystallization of the residue from methanol yielded 17 mg of 4'-amino-5,7-dihydroxy-3-methoxyflavone as pale yellow crystals: $^1$H-nmr spectrum (in DMSO-$d^6$) δ3.75(3H), 5.98(2H), 6.16(1H), 6.41(1H), 6.68(2H), 7.83(2H), 11(1H, broad) and 12.82 ppm (H).

The column was then eluted with acetone-methanol (1:1, v/v) and the eluate, after removal of the solvent, was treated with a solution of diazomethane in ether. After allowing the mixture to stand at room temperature overnight, the solution was evaporated to give 400 mg of solid.

400 mg of said solid were chromatographed on 18 g of silica gel. The column was developed with ethyl acetate/hexane and the eluate was fractioned (each 30 ml). The fractions 3-9 were combined, evaporated under reduced pressure to give yellow crystalline residue. Recrystallization of the residue from methanol yielded 129 mg of 4'-amino-5-hydroxy-3,7-dimethoxyflavone as yellow crystals: m.p. 221° C.

EXAMPLE 16

To an ice-cooled solution containing 200 mg (0.58 mmole) of 4',5-dihydroxy-3,3',7-trimethoxyflavone in 10 ml of pyridine were added 220 mg (1.2 mmole) of hydrochloride of nicotinoyl chloride over 10 minutes, while stirring. After being stirred at room temperature for 3 hours, the mixture was evaporated under reduced pressure to give an oily residue.

The residue was dissolved in 30 ml of chloroform and washed successively, twice with 20 ml each of saturated aqueous sodium bicarbonate and twice with 20 ml each of water. The solution was dried over anhydrous sodium sulphate and then filtered. The filtrate was evaporated to give 200 mg of solid. Recrystallisation of said solid from benzene yielded 170 mg (53% yield) of 3,3',7-trimethoxy-4',5-bis-(nicotinoyloxy)-flavone as colourless needles: m.p. 212°-214° C.

EXAMPLE 17

In a manner analogous to that described in Example 16 except that propionyl chloride was used in place of hydrochloride of nicotinoyl chloride, there was obtained 3,3',7-trimethoxy-4',5-bis-(propionyloxy)-flavone: m.p. 106°-107° C. (Yield 47%).

EXAMPLE 18

In a manner analogous to that described in Example 16 except that acetyl chloride was used in place of hydrochloride of nicotinoyl chloride, crude crystals of 4',5-diacetoxy-3,3',7-trimethoxyflavone were obtained and recrystallized from ethyl acetate/hexane to yield pure product thereof melting at 165°-166° C. (90% yield).

EXAMPLE 19

In a manner analogous to that described in Example 16 except that ethyl chloroformate was used in place of hydrochloride of nicotinoyl chloride, crude crystals of 4',5-bis-(ethoxycarbonyloxy)-3,3',7-trimethoxyflavone were obtained and recrystallised from ethyl acetate/hexane to yield the pure product thereof melting at 106°-107° C. (95% yield).

EXAMPLE 20

To a solution containing 0.2 g of 4',5-dihydroxy-3,3',7-trimethoxyflavone in 3 ml of pyridine was added 0.15 ml of pivalyl chloride, while stirring. The mixture was stirred at room temperature for 3 hours and then heated at 75° C. for 1 hour. After cooling, the mixture was evaporated to give an oily residue.

The residue was dissolved in 10 ml of a mixed solvent of ethanol and hexane (1:1, v/v) and allowed to stand in a refrigerator overnight, during which time crystallisation occurred. The crystals were collected by filtration, washed with hexane and dried. There were obtained 200 mg of 5-hydroxy-3,3',7-trimethoxy-4'-(pivaloyloxy)-flavone as yellow needles: m.p. 163°-164° C.

EXAMPLE 21

To a solution containing 0.2 g of 5-hydroxy-3,3',7-trimethoxy-4'-(pivaloyloxy)-flavone in 3 ml of pyridine was added 0.05 ml of isobutyryl chloride and the mixture was stirred at room temperature for 3 hours. After removal of the solvent by evaporation under reduced pressure, the resulting oily residue was dissolved in 5 ml of a mixed solvent of ethanol and hexane (1:1, v/v). The solution was allowed to stand in a refrigerator overnight, during which time crystallisation occurred. The crystals were collected by filtration, washed with hexane and dried. There were obtained 200 mg of 5-(isobutyryloxy)-3,3',7-trimethoxy-4'-(pivaloyloxy)-flavone as colourless needles: m.p. 151°-152° C.

EXAMPLE 22

In a manner analogous to that described in Example 1 except that 2-ethoxy-2',6'-dihydroxy-4'-methoxyacetophenone was used in place of 2',6'-dihydroxy-2,4'-dimethoxyacetophenone, there was obtained a pale yellow powder of 3-ethoxy-4',5-dihydroxy-3',7-dimethoxyflavone. Crystallisation from ethanol gave the pure product as yellow needles; m.p. 168°-169° C.

EXAMPLE 23

In a manner analogous to that described in Example 1 except that 2',6'-dihydroxy-2-isopropoxy-4'-methoxyacetophenone was used in place of 2',6'-dihydroxy-2,4'-dimethoxyacetophenone, there was obtained a pale yellow powder of 4',5-dihydroxy-3-isopropoxy-3',7-dimethoxyflavone. Crystallisation from ethanol gave the pure product as yellow needles; m.p. 169°-171° C.

The test results of antiviral activity studies on compounds of the invention are described in following Examples 24–28 (in vitro antiviral activity) and Examples 29–32 (in vivo antiviral activity).

EXAMPLE 24

Inhibition of viral cytopathogenic effect

A suspension of HeLa cells ($6 \times 10^4$) was mixed with rhinovirus HGP ($3 \times 10^3$ plaque forming units, PFU) or Coxsackie virus B1 ($3 \times 10^3$ PFU) and was plated in a microtest plate containing the compounds to be tested serially diluted. The cells were then cultured with Eagle's minimum essential medium containing 2% calf serum, 1% tryptose phosphate broth, 100 μg/ml of streptomycin and 20 units/ml of penicillin G. The viral c.p.e. (cytopathogenic effect) was observed by a microscope after 1 day culture at 37° C. for Coxsackie virus infection, and after 2 days culture at 33° C. for rhinovirus infection.

EXAMPLE 25

The test results of Example 24 are shown in Table 1. The antiviral activity of the tested compounds is expressed by the concentration inhibiting the viral c.p.e. by 50% when compared to the control culture ($IC_{50}$).

TABLE 1

| Compound | $IC_{50}$ (μg/ml) | |
|---|---|---|
| | rhinovirus HGP | Coxsackie virus B1 |
| 4',5-dihydroxy-3,3',7-trimethoxyflavone | 0.1 | 0.1–0.2 |
| 4'-hydroxy-3,3',5,7-tetramethoxyflavone | 2–7 | 6–7 |
| 5,7-dihydroxy-3,4'-dimethoxyflavone | 0.5 | >4 |
| 3',5-dihydroxy-3,4',7-trimethoxyflavone | 3 | 3–10 |
| 4',5-dihydroxy-3,7-dimethoxyflavone | 0.1 | 0.1 |
| 5-hydroxy-3,4',7-trimethoxyflavone | 1 | >8 |
| 4',5-dihydroxy-2,',3,7-trimethoxyflavone | 0.3 | 1–3 |
| 4'-acetoxy-5-hydroxy-3,3',7-trimethoxyflavone | 0.5 | 0.25–0.5 |
| 5-hydroxy-4'-(L-lysyloxy-3,3',7-trimethoxyflavone | 0.25 | 0.25 |
| 4'-(β-D-glucopyranosyloky)-5-hydroxy-3,3'7-trimethoxyflavone | 0.25 | 0.25–0.5 |
| 4'-(L-alanyloxy)-5-hydroxy-3,3',7-trimethoxyflavone | 0.5 | 0.25–0.5 |
| 4'-(L-glutaminyloxy)-5-hydroxy-3,3'7-trimethoxyflavone | 0.25–0.5 | 0.25–0.5 |
| 4'-(L-α-glutamyloxy)-5-hydroxy-3,3',7-trimethoxyflavone | 0.25 | 0.25–0.5 |
| 4'(3-carboxy-2,3-dihydroxypropionyloxy)-5-hydroxy-3,3',7-trimethoxyflavone | 0.1–0.2 | 0.1–0.2 |
| 4'-amino-5,7-dihydroxy-3-methoxyflavone | 1–3 | 3–10 |
| 4'-amino-5-hydroxy-3,7-dimethoxyflavone | 3 | 10–30 |
| 3,3',7-trimethoxy-4',5-bis-(nicotinoyloxy)-flavone | 0.3–1 | 0.3–1 |
| 4',5-diacetoxy-3,3',7-trimethoxyflavone | 0.1–0.2 | 0.1–0.2 |
| 4',5-bis-(ethoxycarbonyloxy)-3,3'7-trimethoxyflavone | 0.3–1 | 0.3–1 |
| 5-hydroxy-3,3',7-trimethoxy-4'-(pivaloyloxy)-flavone | 0.3 | 0.3–1 |
| 5-(isobutyryloxy)-3,3',7-trimethoxy-4'-(pivaloyloxy)-flavone | 0.3 | 0.3–1 |
| 3,3'7-trimethoxy-4',5-bis-(propionyloxy)-flavone | 0.1–0.2 | 0.1–1.2 |
| 3-ethoxy-4',5-dihydroxy-3',7-dimethoxyflavone | 0.05–0.1 | 0.05–0.1 |
| 4',5-dihydroxy-3-isopropoxy-3',7-dimethoxyflavone | 0.05–0.1 | 0.05–0.1 |

EXAMPLE 26

The in vitro spectra results from the test of Example 24 for 4',5-dihydroxy-3,3',7-trimethoxyflavone (A) and 4',5-dihydroxy-3,7-dimethoxyflavone (B) are shown in Table 2.

TABLE 2

| virus strain | | Minimum inhibitory concentration (μg/ml) | |
|---|---|---|---|
| | | (A) | (B) |
| rhinovirus type | 1A | 0.03 | 0.03 |
| | 2 | 0.1 | 0.1 |
| | 3 | 0.1 | 0.3 |
| | 4 | 1.0 | 0.3–1.0 |
| | 9 | 0.1 | 0.3 |
| | 13 | 0.3–1.0 | 0.3–1.0 |
| | 14 | 0.1 | 0.3 |
| | 16 | 0.3 | 0.3–1.0 |
| | 17 | 0.3 | 0.1 |
| | 21 | 0.3 | 0.3 |
| | 26 | 0.3 | 0.3 |
| | 30 | 0.03–0.1 | 0.1 |
| | 32 | 0.1 | 0.3 |
| | 34 | 0.3 | 0.3 |
| | 36 | 0.3 | 0.3 |
| | 39 | 0.1 | 0.3 |
| | 44 | 0.05–0.5 | 0.5 |
| | 47 | 0.3 | 0.3 |
| | 50 | 0.3 | 0.3 |
| | 53 | 0.1 | 0.3 |
| | 55 | 0.3 | 0.1–0.3 |
| Coxsackie virus | A21 | 0.1–0.3 | — |
| | B1 | 0.1–0.2 | 0.1 |
| ECHO virus type | 9 | 0.1–0.3 | — |
| | 11 | 0.1–0.3 | — |
| | 12 | 0.1–0.3 | — |
| | 19 | 0.1–0.3 | — |
| poliovirus type | 1 | 0.1–0.3 | — |

EXAMPLE 27

Inhibition of viral replication

The effects of 4',5-dihydroxy-3,3',7-trimethoxyflavone on the replication of rhinoviruses HGP, 1A and Coxsackie virus B1 in HeLa cells were tested. Monolayers of said cells ($4 \times 10^5$) were infected with each virus ($4 \times 10^4$ PFU). Thereafter, said cells were washed with Eagle's minimum essential medium and further cultured with said medium containing 2% calf serum, 1% tryptose phosphate broth, 100 μg/ml of strermptomycin sulfate, 20 units/ml of penicillin G and 4',5-dihydroxy-3,3',7-trimethoxyflavone at various doses. The total yields of rhinoviruses and Coxsackie virus replicated in the cultures were assayed 2 and 1 days after infection, respectively.

EXAMPLE 28

The test results of Example 27 are shown in FIG. 1, demonstrating that 4',5-dihydroxy-3,3',7-trimethoxyflavone reduces the viral replication quite considerably in concentrations of 0.5 to 2 μg/ml, at which dose HeLa cell growth is not affected.

EXAMPLE 29

Anti-Coxsackie virus activity

Compounds of the present invention were tested for their antiviral activities against lethal infection of Coxsackie virus B1 in mice. The ddy mice weighing 15 g were infected intraperitoneally with about the tenfold $LD_{50}$ of Coxsackie virus B1. The infected mice were then treated 4 or 9 times, 2, 6, 18 and 30 hour or 0, 2, 5, 18, 24, 42, 48, 66 and 72 hours after infection with the compounds intraperitoneally (i.p.), intravenously (i.v.) or orally (p.o.), and the survivals were recorded up to 21 days.

EXAMPLE 30

The test results of Example 29 are shown in Table 3. Control mice treated with phosphate buffered saline solution or water dried at 3 to 5 days after infection. Doses are expressed in milligrams of active ingredient per kilogram of body weight of mouse.

TABLE 3

| Compound | Dose | Route | Survival [%] |
|---|---|---|---|
| 4',5-dihydroxy-3,3',7-trimethoxyflavone | 20 mg/kg × 9 | i.p. | 20 |
| | 10 mg/kg × 9 | " | 10 |
| | 40 mg/kg × 9 | p.o. | 30 |
| | 20 mg/kg × 9 | " | 10 |
| 5-hydroxy-4'-(L-lysyloxy)-3,3',7-trimethoxyflavone | 10 mg/kg × 9 | i.v. | 54 |
| 4'-(L-alanyloxy)-5-hydroxy-3,3',7-trimethoxyflavone | 10 mg/kg × 9 | i.v. | 42 |
| 4'-(L-glutaminyloxy)-5-hydroxy-3,3',7-trimethoxyflavone | 10 mg/kg × 9 | i.v. | 54 |
| 3,3'7-trimethoxy-4',5-bis(nicotinoyloxy)flavone | 20 mg/kg × 9 | p.o. | 30 |
| | 10 mg/kg × 9 | " | 40 |
| 4',5-diacetoxy-3,3'7-trimethoxyflavone | 20 mg/kg × 9 | i.p. | 67 |
| | 10 mg/kg × 9 | " | 54 |
| | 80 mg/kg × 4 | p.o. | 60 |
| | 40 mg/kg × 4 | " | 50 |
| | 40 mg/kg × 9 | " | 50 |
| | 20 mg/kg × 9 | " | 20 |
| 4',5-bis(ethoxycarbonyloxy)-3,3',7-trimethoxyflavone | 20 mg/kg × 9 | p.o. | 30 |
| | 10 mg/kg × 9 | " | 30 |
| 5-(isobutyryloxy)-3,3',7-trimethoxy-4'-(pivaloyloxy)flavone | 20 mg/kg × 9 | p.o. | 40 |
| | 10 mg/kg × 9 | " | 30 |
| none | — | — | 0 |

EXAMPLE 30

The following Table 4 shows the antiviral activity of 4',5-diacetoxy-3,3',7-trimethoxyflavone against the infection with various doses of Coxsackie virus B1 in mice. The compound suspended in a solution of 0.5% carboxymethylcellulose was administered orally at 0, 2, 5, 18, 24, 42, 48, 66 and 72 hours after lethal infection with Coxsackie virus B1 (i.p.) The survivors were recorded on day 21.

TABLE 4

| Administration with said compound | Survivors/total Infection with Coxsackie virus B1 ($LD_{50}$) | | | |
|---|---|---|---|---|
| | $2.5_x$ | $10_x$ | $40_x$ | $160_x$ |
| 40 mg/kg × 9 | 4/7 | 3/7 | 2/7 | 2/7 |
| 20 mg/kg × 9 | 3/7 | 2/7 | 1/7 | 1/7 |
| 10 mg/kg × 9 | 2/7 | 1/7 | 0/7 | 0/7 |
| 0 | 0/7 | 0/7 | 0/7 | 0/7 |

EXAMPLE 31

Anti-influenzavirus activity

4',5-Diacetoxy-3,3',7-trimethoxyflavone was treated for its activity against influenzavirus A2/Adachi in mice. The ddy mice weighing 12 g were infected intranasally by about 5 times the $LD_{50}$ dosage of influenzavirus. The mice were administered 9 times with the compound intraperitoneally and the survivors were recorded up to 21 days. The results are tabulated in Table 5.

TABLE 5

| Treatment | | Survivals (%) | |
|---|---|---|---|
| phosphate buffered saline solution | | 0/8 | (0) |
| 4',5-diacetoxy-3,3',7-trimethoxyflavone | | | |
| 20 mg/kg × 9,* | i.p. | 2/7 | (29) |
| 40 mg/kg × 9, | i.p. | 3/8 | (38) |
| amantadine | | | |
| 20 mg/kg × 9 | i.p. | 0.6 | (0) |
| 40 mg/kg × 9, | i.p. | 2/7 | (29) |

*administered at 0.5 hours before and 4, 8, 12, 24, 28, 32, 48 and 56 hours after infection As shown in Table 5, the antiviral activity of the tested compound is at least as high as that of amantadine, a conventional anti-influenzavirus agent.

EXAMPLE 32

The following Table 6 shows data on the compounds of the invention concerning acute toxicity in mice.

TABLE 6

| Compound | $LD_{50}$ (mg/kg)[1] | |
|---|---|---|
| | i.p.[2] | p.o.[3] |
| 4',5-dihydroxy-3,3',7-trimethoxyflavone | >1,000 | >5,000 |
| 5-hydroxy-4'-(L-lysyloxy)-3,3',7-trimethoxyflavone | 1,000 | >5,000 |
| 4'-(L-alanyloxy)-5-hydroxy-3,3',7-trimethoxyflavone | >1,000 | >5,000 |
| 4'-(L-glutaminyloxy)-5-hydroxy-3,3',7-trimethoxy- | | |

TABLE 6-continued

| Compound | LD$_{50}$ (mg/kg)[1] | |
|---|---|---|
| | i.p.[2] | p.o.[3] |
| flavone 4',5-diacetoxy-3,3',7- | >1,000 | >5,000 |
| trimethoxyflavone | >1,000 | >5,000 |

[1]The ddy mice weighing 15-20 g were administered with a single dose of the compound. The survivors were recorded on day 21.
[2]The compounds were dissolved in dimethyl sulfoxide.
[3]The compounds were suspended in a solution of 0.5% carboxymethylcellulose and sonicated.

We claim:
1. An anti-enteroviral composition comprising:
   (a) as an active ingredient a compound of the formula:

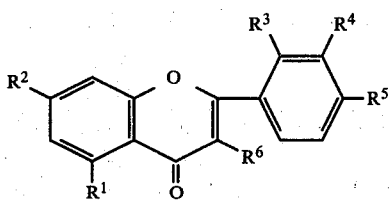

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof,
in an amount which is effective as an anti-enteroviral agent; and
   (b) a pharmaceutically acceptable carrier material.

2. An anti-rhinoviral composition comprising:
   (a) as an active ingredient a compound of the formula:

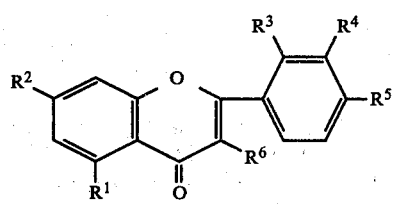

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof,
in an amount which is effective as an anti-rhinoviral agent; and
   (b) a pharmaceutically acceptable carrier material.

3. An anti-influenzaviral composition comprising:
   (a) as an active ingredient a compound of the formula:

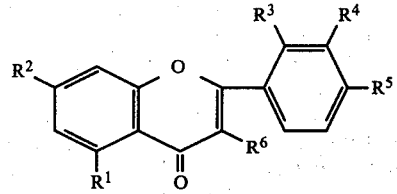

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof,
in an amount which is effective as an anti-influenzaviral agent; and
   (b) a pharmaceutically acceptable carrier material.

4. The composition of claim 1, 2 or 3 wherein $R^5$ is hydroxy.

5. The composition of claim 4 wherein the compound is 3-ethoxy-4',5-dihydroxy-3',7-dimethoxyflavone.

6. The composition of claim 4 wherein the compound is 4',5-dihydroxy-3-isopropoxy-3',7-dimethoxyflavone.

7. The composition of claim 4 wherein the compound is 4',5-dihydroxy-3,3',7-trimethoxyflavone.

8. The composition of claim 4 wherein the compound is 4'-hydroxy-3,3',5,7-tetramethoxyflavone.

9. The composition of claim 4 wherein the compound is 4',5-dihydroxy-3,7-dimethoxyflavone.

10. The composition of claim 4 wherein the compound is 4',5-dihydroxy-2',3,7-trimethoxyflavone.

11. The composition of claim 1, 2 or 3 wherein $R^5$ is lower alkoxy.

12. The composition of claim 11 wherein the compound is 5,7-dihydroxy-3,4'-dimethoxyflavone.

13. The composition of claim 11 wherein the compound is 3',5-dihydroxy-3,4',7-trimethoxyflavone.

14. The composition of claim 11 wherein the compound is 5-hydroxy-3,4',7-trimethoxyflavone.

15. The composition of claim 1, 2 or 3 wherein $R^5$ is lower alkanoyloxy.

16. The composition of claim 15 wherein the compound is 4'-acetoxy-5-hydroxy-3,3',7-trimethoxyflavone.

17. The composition of claim 15 wherein the compound is 5-hydroxy-3,3',7-trimethoxy-4'-(pivaloyloxy)-flavone.

18. The composition of claim 15 wherein the compound is 5-(isobutyryloxy)-3,3',7-trimethoxy-4'-(pivaloyloxy)-flavone.

19. The composition of claim 15 wherein the compound is 3,3',7-trimethoxy-4',5-bis-(propionyloxy)-flavone.

20. The composition of claim 15 wherein the compound is 4',5-diacetoxy-3,3',7-trimethoxyflavone.

21. The composition of claim 1, 2 or 3 wherein R⁵ is aminoacyloxy.

22. The composition of claim 21 wherein the compound is 5-hydroxy-4'-(L-lysyloxy)-3,3',7-trimethoxyflavone.

23. The composition of claim 21 wherein the compound is 4'-(L-alanyloxy)-5-hydroxy-3,3',7-trimethoxyflavone.

24. The composition of claim 21 wherein the compound is 4'-(L-glutaminyloxy)-5-hydroxy-3,3',7-trimethoxyflavone.

25. The composition of claim 21 wherein the compound is 4'-(L-α-glutamyloxy)-5-hydroxy-3,3',7-trimethoxyflavone.

26. The composition of claim 1, 2 or 3 wherein R⁵ is glycosyloxy.

27. The composition of claim 26 wherein the compound is 4'-(β-D-glucopyranosyloxy)-5-hydroxy-3,3',7-trimethoxy-flavone.

28. The composition of claim 1, 2 or 3 wherein R⁵ is a hydroxy-substituted dicarboxylic acid residue.

29. The composition of claim 28 wherein the compound is 4'-(3-carboxy-2,3-dihydroxypropionyloxy)-5-hydroxy-3,3',7-trimethoxyflavone.

30. The composition of claim 1, 2 or 3 wherein R⁵ is amino.

31. The composition of claim 30 wherein the compound is 4'-amino-5,7-dihydroxy-3-methoxyflavone.

32. The composition of claim 30 wherein the compound is 4'-amino-5-hydroxy-3,7-dimethoxyflavone.

33. The composition of claim 1, 2 or 3 wherein R⁵ is nicotinoyloxy.

34. The composition of claim 33 wherein the compound is 3,3',7-trimethoxy-4',5-bis-(nicotinoyloxy)-flavone.

35. The composition of claim 1, 2 or 3 wherein R⁵ is lower alkoxycarbonyloxy.

36. The composition of claim 35 wherein the compound is 4',5-bis-(ethoxycarbonyloxy)-3,3',7-trimethoxyflavone.

37. The composition of claim 1, 2 or 3 wherein compound I amounts to about 0.001% to about 70% by weight of the composition.

38. A compound of the formula:

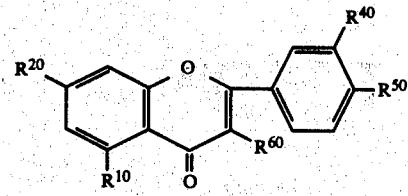

II wherein R¹⁰ is hydroxy, lower alkanoyloxy, lower alkoxycarbonyloxy or nicotinoyloxy; R²⁰ is hydroxy or lower alkoxy;
R⁴⁰ is hydrogen or lower alkoxy; R⁵⁰ is hydroxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and R⁶⁰ is lower alkoxy, with the proviso that when R¹⁰ is acetoxy, R⁵⁰ is other than acetoxy and with the further proviso that when R⁵⁰ is hydroxy, R⁶⁰ is other than methoxy;
or pharmaceutically acceptable salts thereof.

39. The compound of claim 38 wherein R⁵⁰ is hydroxy.

40. The compound of claim 39, 3-ethoxy-4',5-dihydroxy-3',7-dimethoxyflavone.

41. The compound of claim 39, 4',5-dihydroxy-3-isopropoxy-3',7-dimethoxyflavone.

42. The compound of claim 38 wherein R⁵⁰ is lower alkanoyloxy.

43. The compound of claim 42, 4'-acetoxy-5-hydroxy-3,3',7-trimethoxyflavone.

44. The compound of claim 42, 5-hydroxy-3,3',7-trimethoxy-4'-(pivaloyloxy)-flavone.

45. The compound of claim 42, 5-(isobutyryloxy)-3,3',7-trimethoxy-4'-(pivaloyloxy)-flavone.

46. The compound of claim 42, 3,3',7-trimethoxy-4',5-bis-(propionyloxy)-flavone.

47. The compound of claim 38 wherein R⁵⁰ is aminoacyloxy.

48. The compound of claim 47, 5-hydroxy-4'-(L-lysyloxy)-3,3',7-trimethoxyflavone.

49. The compound of claim 47, 4'-(L-alanyloxy)-5-hydroxy-3,3',7-trimethoxyflavone.

50. The compound of claim 47, 4'-(L-glutaminyloxy)-5-hydroxy-3,3',7-trimethoxyflavone.

51. The compound of claim 47, 4'-(L-α-glutamyloxy)-5-hydroxy-3,3',7-trimethoxyflavone.

52. The compound of claim 38 wherein R⁵⁰ is glycosyloxy.

53. The compound of claim 52, 4'-(β-D-glucopyranosyloxy)-5-hydroxy-3,3',7-trimethoxyflavone.

54. The compound of claim 38 wherein R⁵⁰ is a hydroxy-substituted dicarboxylic acid residue.

55. The compound of claim 54, 4'-(3-carboxy-2,3-dihydroxy propionyloxy)-5-hydroxy-3,3',7-trimethoxyflavone.

56. The compound of claim 38 wherein R⁵⁰ is amino.

57. The compound of claim 56, 4'-amino-5,7-dihydroxy-3-methoxyflavone.

58. The compound of claim 56, 4'-amino-5-hydroxy-3,7-dimethoxyflavone.

59. The compound of claim 38 wherein R⁵⁰ is nicotinoyloxy.

60. The compound of claim 59, 3,3',7-trimethoxy-4',5-bis-(nicotinoyloxy)-flavone.

61. The compound of claim 38 wherein R⁵⁰ is lower alkoxycarbonyloxy.

62. The compound of claim 61, 4',5-bis-(ethoxycarbonyloxy)-3,3',7-trimethoxyflavone.

63. A method for treating a mammal infected by an enterovirus comprising administering to said mammal a compound of the formula:

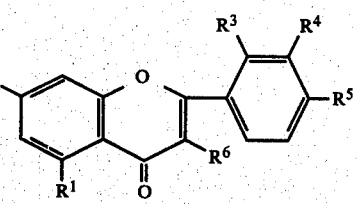

I wherein R¹ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof, in an amount which is effective as an anti-enteroviral agent.

64. A method for treating a mammal infected by a rhinovirus comprising administering to said mammal a compound of the formula:

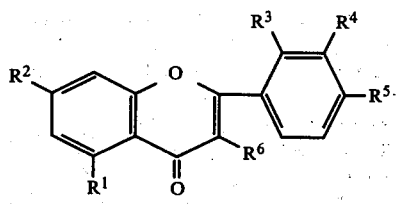

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof, in an amount which is effective as an anti-rhinoviral agent.

65. A method for treating a mammal infected by an influenzavirus comprising administering to said mammal a compound of the formula:

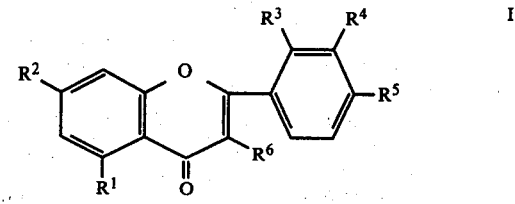

wherein $R^1$ is hydroxy, lower alkoxy, lower alkanoyloxy, lower alkoxycarbonyloxy or nicotinoyloxy; $R^2$ is hydroxy or lower alkoxy; $R^3$ is hydrogen or lower alkoxy; $R^4$ is hydrogen, hydroxy or lower alkoxy; $R^5$ is hydroxy, lower alkoxy, lower alkanoyloxy, aminoacyloxy where its acyloxy group has 2 to 10 carbon atoms, glycosyloxy which is derived from a monosaccharide of 5 to 7 carbon atoms, a hydroxy-substituted dicarboxylic acid residue where its dicarboxylic acid group has 2 to 8 carbon atoms, amino, nicotinoyloxy or lower alkoxycarbonyloxy and $R^6$ is lower alkoxy, or pharmaceutically acceptable salts thereof, in an amount which is effective as an anti-influenzaviral agent.

66. The method of claim 63, 64 or 65 wherein the compound is 3-ethoxy-4',5-dihydroxy-3',7-dimethoxyflavone.

67. The method of claim 66 wherein the compound is administered at a daily dose of about 1 mg. to about 100 mg. of compound per kilogram of body weight of the mammal.

* * * * *